(12) United States Patent
Knauss

(10) Patent No.: US 9,355,787 B2
(45) Date of Patent: May 31, 2016

(54) METHOD OF FORMING RIGID IMIDE MATERIAL FROM SOLUBLE AMIDE ESTER FUNCTIONALIZED PRECURSORS

(71) Applicant: Colorado School of Mines, Golden, CO (US)

(72) Inventor: Daniel M. Knauss, Golden, CO (US)

(73) Assignee: Colorado School of Mines, Golden, CO (US)

( * ) Notice: Subject to any disclaimer, the term of this patent is extended or adjusted under 35 U.S.C. 154(b) by 0 days.

(21) Appl. No.: 14/169,089

(22) Filed: Jan. 30, 2014

(65) Prior Publication Data

US 2014/0209879 A1 Jul. 31, 2014

Related U.S. Application Data

(60) Provisional application No. 61/758,431, filed on Jan. 30, 2013.

(51) Int. Cl.

| | | |
|---|---|---|
| *C09D 177/12* | (2006.01) | |
| *H01G 9/20* | (2006.01) | |
| *C07C 67/08* | (2006.01) | |
| *H01L 51/44* | (2006.01) | |
| *H01L 51/00* | (2006.01) | |
| *C09D 179/08* | (2006.01) | |
| *C08G 73/10* | (2006.01) | |

(52) U.S. Cl.
CPC *H01G 9/20* (2013.01); *C07C 67/08* (2013.01); *C08G 73/105* (2013.01); *C08G 73/1007* (2013.01); *C08G 73/1028* (2013.01); *C08G 73/1032* (2013.01); *C08G 73/1067* (2013.01); *C08G 73/1071* (2013.01); *C09D 179/08* (2013.01); *H01L 51/0003* (2013.01); *H01L 51/0053* (2013.01); *H01L 51/448* (2013.01); *C07C 2103/52* (2013.01); *Y02E 10/542* (2013.01); *Y02E 10/549* (2013.01); *Y10T 428/31721* (2015.04)

(58) Field of Classification Search
CPC .................................................. C09D 177/12
USPC .................. 427/350, 385.5; 428/473; 560/80; 524/600; 257/40
See application file for complete search history.

(56) References Cited

U.S. PATENT DOCUMENTS

| 5,029,979 | A | * | 7/1991 | Robello et al. | 385/141 |
| 5,397,841 | A | * | 3/1995 | DuBois et al. | 525/227 |
| 5,824,744 | A | * | 10/1998 | Gagne et al. | 525/143 |
| 2005/0243252 | A1 | * | 11/2005 | Matsuoka | 349/117 |

OTHER PUBLICATIONS

Charlier et al. "High temperature polymer nanofoams based on amorphous, high Tg polymides," Polymer, Mar. 1995, vol. 36, No. 5, pp. 987-1002.
Volksen et al. "Chemistry and Characterization of Polyimides Derived from Poly(Amic Alkyl Esters)," Materials Research Society Symposium Proceedings, 1991, vol. 227, pp. 23-34.

* cited by examiner

*Primary Examiner* — John P Dulka
(74) *Attorney, Agent, or Firm* — Sheridan Ross P.C.

(57) ABSTRACT

This invention relates to a method for making soluble precursors to imides, polyimides, and polymers containing imide groups, and a method of making thin films of the same by solution casting and then removing the solubilizing group to produce thermally stable and insoluble materials.

20 Claims, 11 Drawing Sheets indicates that either isomer is possible; R = aliphatic group; X = polymerizable component for aryl-aryl coupling.

(IIA') - PI OF (IIA) THERMALLY IMIDIZED TO 300 °C EXTERNALLY
(IIA") - PI OF (IIA) THERMALLY IMIDIZED TO 250 °C EXTERNALLY
(IIA*) - PAE OF (IIA) HEATED IN STEP-WISE INCREMENTS IN SEIKO TGA SSC/5200

(IIA') - PAE OF (IIA)
(IIA) - PI OF (IIA) THERMALLY IMIDIZED TO 300 °C EXTERNALLY

[a] - UV-VIS SPECTROSCOPY OF NAPTHALENE DIESTER - DIACID IN DMSO
[b] - UV - VIS SPECTROSCOPY OF PERYLENE DIESTER - DIACID IN DMSO

PAE OF (IA)* & (IIA)* UNDER VARIOUS EXCITATION WAVELENGTH IN DMSO SOLUTION AT CONC. OF 1x10⁻⁴ mol/L (IA*), (IIA*) - PAE OF (IA), (IIA) IN DMSO
(IA), (IIA) - PI OF (IA), (IIA) SPIN COATED ON QUARTZ SLIDE

METHOD OF FORMING RIGID IMIDE MATERIAL FROM SOLUBLE AMIDE ESTER FUNCTIONALIZED PRECURSORS

CROSS-REFERENCE TO RELATED APPLICATIONS

This application claims the benefit of U.S. Provisional Patent Application Ser. No. 61/758,431, filed Jan. 30, 2013, the entire disclosure of which is hereby incorporated herein by reference.

TECHNICAL FIELD

This invention relates to a method for making soluble precursors to imides, polyimides, and polymers containing imide groups, and a method of making thin films of the same by solution casting and then removing the solubilizing group to produce thermally stable and insoluble materials.

BACKGROUND OF INVENTION

Aromatic polyimides have attracted a lot of interest over the last few decades, owing to their exceptionally high chemical, photochemical and thermo-oxidative stability. These unique properties make them suitable for a wide range of applications including microelectronics, aerospace, liquid crystal displays and photoelectronics. Completely aromatic polyimides, however, lack solution processibility and consequently are difficult to work with. To overcome this problem, a two stage polycondensation reaction is employed, which involves the formation of processable polyamideacids (PAA) as precursor, followed by cyclization via thermal or chemical routes to form the final insoluble polyimide. However, polyamide-acids are unstable; this inherent disadvantage limits their industrial use. This could be overcome by polyamide-ester as precursors wherein alkyl esters are incorporated, which increases the stability and provides additional synthetic flexibility. These polyamide-esters have longer shelf lives, can be resolubilized into a suitable solvent and thermally imidized. This alternative approach now allows the synthesis of otherwise inaccessible polyimide systems in high molecular weight.

Molecules with extended pi-conjugation, including pi-conjugated polymers and polymers with acene groups like perylene or naphthalene are known to display useful properties for optoelectronic applications including but not limited to photovoltaics, light emitting diodes, and field effect transistors. The extended pi-conjugation or rigidity of the molecules negatively affects the solubility. Straight or branched alkyl chains or alkyl ether chains are often attached to the pi-conjugated molecule through direct attachment or ether, ester, imide or other linkages. For example, poly(3-hexylthiophene), poly(2,5-alkoxy phenylene vinylene)s like poly[2-methoxy-5-(2'-ethylhexyloxy)-p-phenylene vinylene], or poly(2,5-dialkyl-1,4-phenylene)s are pi-conjugated polymers that are soluble in, and therefore solution processable from common solvents, where the base polymer without the solubilizing side chain is insoluble.

One relevant example of a pi-conjugated polymer is one that contains alkyl imide solubilizing side chains where the pi-conjugated polymer can be a polythiophene, a polyphenylene, a polynaphthalene or similar polymer where the alkyl imide is attached as a pendent group for both an electron withdrawing effect and for an increase in solubility. In the case of a polythiophene backbone, the alkylimide pendent material has shown excellent properties as a donor material in photovoltaics with the group named as thieno[3,4-c]pyrrole-4,6-dione (TPD). The acene groups like perylene and naphthalene are also pi-conjugated molecules that display reduced solubility especially when incorporated into larger molecules. The solubility of perylene in particular has often been improved by attaching alkyl chains to various positions on the ring structure or as alkyl imide chains from the perylene dianhydride. Perylene and naphthalene dianhydrides are difunctional molecules that can be reacted through their anhydride groups into diimides or polyimides, however the solubility of the resulting diimides or polyimides is severely minimized if reacted with other rigid aromatic molecules.

Based on the imide structure of the polyimides, they can be broadly classified into two classes: five- and six-membered. Polymers with six-membered imide rings such as polynaphthalinimides (PNIs) and polyperyleneimides (PPIs) are thermally and chemically more stable compared to the five-membered phthalic polyimides. PPIs have recently emerged as a new class of n-type polymers for application in polymer solar cells. 3,4,9,10-perylene tetracarboxylic dianhydride (PTDA) and 1,4,5,8-naphthalenetetracarboxylic dianhydride (NTDA) are two commonly found starting materials from which six-membered polyimide could be obtained. The extended pi-conjugation found in these dianhydrides makes them good electron acceptors and conductors. Their planar structure makes it possible to synthesize well ordered thin films on various substrates increasing luminescence and charge transfer properties. However, due to the rigid planar nature of the molecule, incorporating it into a polymer has been rather difficult and, consequently, less studied. Bisimides and polyimides incorporating perylene and naphthalene units for better performance in opto-electronics have been reported in the literature. Similarly, perylene based polyimides with different alkyl chain lengths ranging from $C_3$ to $C_{12}$ and their structural characteristics have been reported. It has often been observed that synthesis of perylene and naphthalene moiety containing polyimides that are solution processable in their polyamide-ester form are highly desirable for incorporation in optoelectronic materials.

Rigid molecules like pi-conjugated polymers and polyimides often suffer from a decreased solubility compared to more flexible molecules. Solubilization of rigid molecules is important because the molecules often need to be dissolved in a solvent for their synthesis, and the processing of molecules from solution is important for the preparation of films and fibers. Two methods have been shown to be effective for the solution synthesis and/or processing of rigid molecules. The first method is the attachment of flexible alkyl chains to increase the solubility of rigid molecules. The second method is to prepare a soluble precursor molecule that upon thermal or other reaction results in the formation of the rigid and less soluble molecule. Each method has advantages and drawbacks with numerous examples that can be found in the literature. Alkyl side chains can promote solubility but also introduce problems in efficient packing or ultimate thermal stability in the solid state. Soluble precursor molecules can undergo unwanted side reactions or incomplete reaction upon thermal conversions to rigid molecules.

SUMMARY

It is an aspect of the present invention to provide a method to produce a soluble material by the formation of an ortho- or alpha- (in the case of naphthalene and perylene) substituted ester and amide, where the ester group is designed to confer solubility and the amide group is designed to be an aryl amide has been developed. The soluble material is then solution processed into a film or other form such as fiber for application and subsequently converted into an aryl imide group with loss of the solubilizing ester group through reaction of the amide nitrogen with the ester. The resulting aryl imide is a thermally stable group compared to the alkyl group and is expected to confer electronic properties on the molecule and change the packing of the molecules.

The method, in one embodiment includes a description of how to solubilize 3,4,9,10-perylene tetracarboxylic dianhydride (PTDA) and 1,4,5,8-naphthalenetetracarboxylic dianhydride (NTDA) via formation of diester-diacids. The procedure involves incorporation of long chain alkyl esters to the dianhydrides forming diester-diacids. Since PTDA is found to be insoluble in all solvents, it is paramount to form diester-diacids and react that with the diamines instead of the anhydrides themselves. Furthermore, as PTDA does not dissolve in alcohols, an alternative procedure wherein sodium alkoxide of the alcohols is reacted with PTDA to obtain the diester-diacids. The result is increased solubility of monomer in polar aprotic solvents like DMSO and NMP. These are then reacted with aromatic diamines under the Yamazaki-amidation conditions resulting in polyamide-esters (PAEs). The PAEs remain soluble during reaction long enough to form high molecular weight polymers. The PAEs are then precipitated and re-solubilized in polar aprotic solvents.

It is another aspect of the present innovation to provide a method for solubilizing rigid rod molecules through the formation of a soluble precursor molecule that after solution processing can be thermally converted to an insoluble and infusible rigid molecule. In one embodiment, the invention makes use of ortho- or alpha-substituted amide esters wherein the ester is comprised of a flexible alkyl chain or other similar solubilizing group and the amide is an aromatic amide. The soluble polymer with both aryl amide and alkyl ester groups is processed from solution to form films or fibers and is then subjected to a thermal imidization reaction whereby an aryl imide is produced with the loss of the alkyl group as an alcohol. The imide formation between an aryl amide and an alkyl ester is known to be a high yielding reaction to produce a thermally stable aryl imide group.

In one embodiment, thin films of imide-precursor polymers may be cast from solution, or by spin-coating on various substrates. The thin films have thermal, optical, electrical, electro-optical, and electrochemical properties which may be useful in the preparation of devices such as, but not limited to organic electronics, organic photovoltaics, flexible and/or transparent thin films, electro-optically active materials, dye-sensitized solar cells, bulk heterojunction cells, light emitting diodes, and various organic electronics. The resulting imides and polyimides can be designed to have high temperature stability to be compatible with high temperature processing potentially allowing the integration of the thin films into standard semiconductor processing approaches.

One aspect of the invention is that polyimide precursors can be solubilized, polymerized, cast into films, and imidized to make polyimide or imide-containing polymers that can be used for various electronic and optical applications, as well as, rigid polymers similar to other polyimides. The reaction requires high temperatures to imidize and remove alcohol, which results in thermally stable films. Many procedures are possible, which make many different polyimide or imide-containing polymers possible for a wide variety of applications.

In another embodiment of the invention, an insoluble and intractable, thermally stable imide-functionalized film of particular compositions can be produced. The way this film is produced is through a soluble precursor. That soluble precursor contains imide precursors (aliphatic ester and aryl amide functional groups) adjacent to each other. Upon thermal treatment, the ester and amide react with each other to form an aryl imide with concomitant loss of the alkyl group as an alcohol.

In yet another embodiment, the imide becomes part of the main chain as in the production of polyimides containing PTDA or NTDA. In this case, the soluble material is a poly (aryl amide) with pendent alkyl ester functional groups that confer solubility. Upon thermal treatment, the material becomes a true polyimide where the imide functional group links each repeat unit along the main chain.

In a further embodiment, the imide becomes a pendent functional group on a material that has aryl-aryl bonds (a conjugated molecule/polymer) along the main chain. The pendent alkyl ester and pendent aryl amide groups confer solubility allowing solution processing to form a film. In this case, thermal processing results in loss of the alkyl ester as an alcohol and formation of a pendent imide group. The resulting film has material properties that include being thermally stable, insoluble, intractable, and with improved chain-chain packing which results in improved electronic properties.

In another embodiment, it is recognized that the final film, or fiber, cannot be directly produced because it would be insoluble and intractable, not allowing the material to be made. However, the present invention provides a method that allows the preparation of soluble precursors to the desired materials in film form. The precursors can be used in solution with any solvent in which they are soluble, can be converted to films or fibers, and then can be thermally treated to result in the final desired structures. There are two types of materials: 1) the imide group is part of the linking group between connecting units (PTDA and NTDA polyimides or even smaller molecules/oligomers containing PTDA or NTDA) and 2) the imide is a pendent group to aryl-aryl coupled units, where the imide is part of an aryl (phenyl, naphthyl) or heteroaryl group (thiophene, or other). The alkyl ester is the important component for the solubility. The alkyl ester needs to be long enough to confer solubility but short enough that upon loss as an alcohol it is easily removed from the system. That means probably longer than butyl and probably shorter than decyl with hexyl being a good tradeoff. The alkyl ester could also be branched or contain other functional groups to improve solubility.

DESCRIPTION

Figure 1:
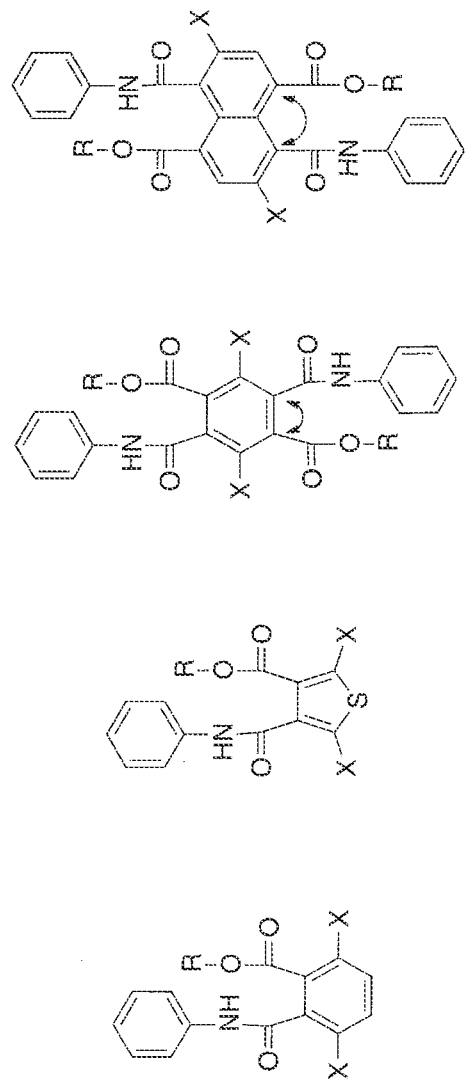
FIG. 1: depicts example monomers with amide/ester imide precursors.

The present invention relates to a method to solubilize rigid or conjugated molecules. PTDA and NTDA are examples of rigid molecules that can be solubilized via formation of diester-diacids. One embodiment of the procedure involves incorporation of long chain alkyl esters, with potential alkyl chain lengths ranging from $C_3$ to $C_{12}$, to the dianhydrides forming diester-diacids. While not wishing to be bound by any theory, it is believed that it is the aliphatic ester group that promotes solubility for both the monomer and resulting polyimide binder, and that the smallest alkyl chain length that effectively promotes solubility is optimal. Since PTDA is found to be insoluble in all solvents, it is paramount to form diesters-diacid and react that with the diamines instead of the anhydrides themselves. Furthermore, as PTDA does not dissolve in alcohols, a second embodiment of the procedure is provided wherein sodium alkoxides of the alcohols are reacted with PTDA to obtain the diester-diacids. The reaction to prepare the diester-diacid results in increased solubility of the monomers in polar aprotic solvents like, but not limited to, dimethyl sulfoxide (DMSO) and N-Methyl-2-pyrrolidone (NMP). Additional polar aprotic solvents that may be used in the reactions include, but are not limited to, tetrahydrofuran (THF), ethyl acetate (EtOAc), acetone, dimethylformamide (DMF), and acetonitrile (MeCN). The monomers are then reacted with aromatic diamines, such as, but not limited to 4,4'Oxydianiline (ODA). The reactions can be performed under, but are not limited to, the Yamazaki-amidation conditions, which result in polyamide-esters (PAEs). The PAEs remained soluble during reaction long enough to form high molecular weight polymers. The PAEs are then precipitated and re-solubilized in polar aprotic solvents.

The imide side group is typically a long-chain aliphatic group in order to improve the solubility and therefore the solution processibility of the polymer material. While not wishing to be bound by any theory, in addition to solubility improvement, the imide side group provides an electron accepting nature to the molecule. In the present invention, precursors to an imide group are demonstrated to effect solubility of the conjugated polymer. The imide precursor is an arylamide in a position ortho (or alpha in the case of naphthalene) to an aliphatic ester. The size and composition of the aliphatic ester group can be varied from methyl to octyl or bigger and with or without branching in order to tune the solubility of the monomers and polymers. Upon ring closure through thermal and/or chemical methods, an arylimide can be produced through attack of the amide nitrogen on the ester carbonyl with loss of the aliphatic alcohol. The resulting imide is thermally stable compared to an aliphatic imide and the solubility of the resulting polymer is greatly decreased. In addition, the packing of the polymer molecules and the electronic properties will be affected compared to an aliphatic imide. A variety of polymers and copolymers can be produced using this method of solubilization to result in polymers with donor and acceptor components. The aryl component can be a simple phenyl group or it can be some other aromatic group such as an acene, oligophenyl, or heteroaryl group. The nature of the aryl group could allow tuning of the electronic properties.

Figure 2:
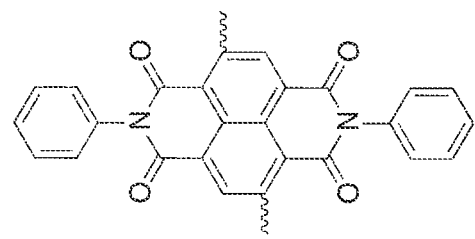
FIG. 2: depicts examples of resulting imide polymer or copolymer units after film formation and imidization.
Figure 2:
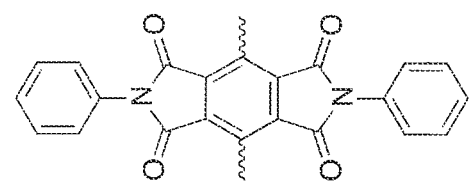
Figure 2:
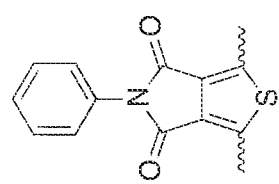
Figure 2:
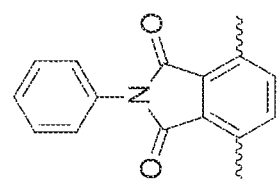
Figure 10:
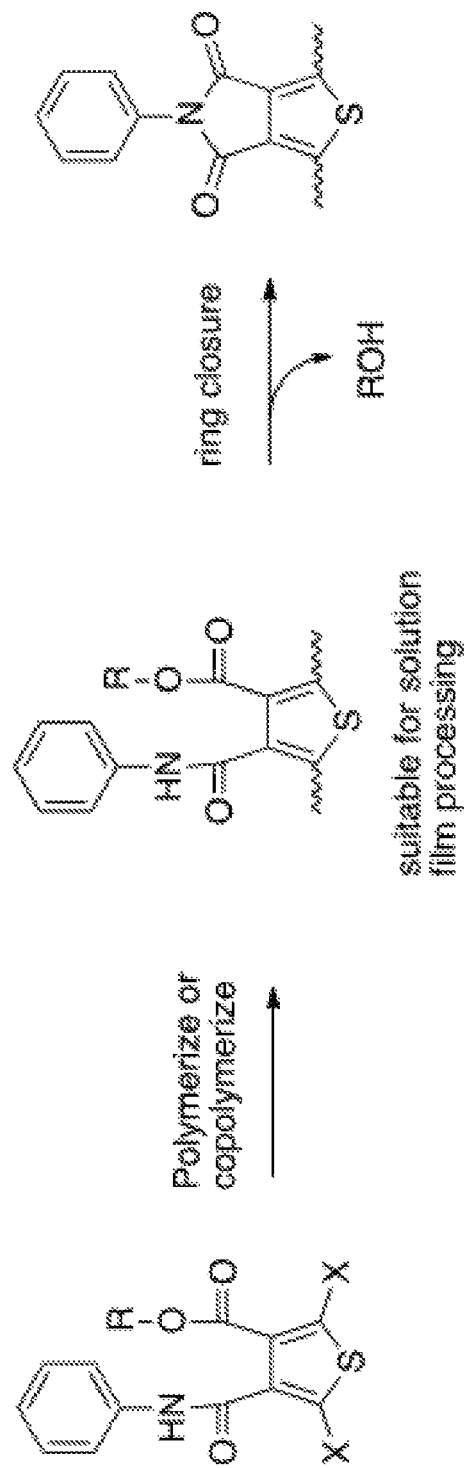
FIG. 10: illustrates an example of the polymerization and subsequent imidization of a thiophene based monomer.

Examples of imide precursor monomers are presented in FIG. 1 and a generalized scheme for polymerization and imide formation is provided using a thiophene monomer in FIG. 10. Various comonomers can be copolymerized with the precursor monomers to affect the final electronic properties of the polymers. FIG. 2 provides examples of polymer repeat units (or component units in the case of copolymers) from each of the example monomers from FIG. 1.

Films of varying thicknesses of polyimides may be cast from solution, or by spin-coating on various substrates. The polyamide esters (PAEs) and polyamides (PIs) can be dissolved in polar aprotic solvents including, but not limited to, DMSO and NMP at temperatures ranging from about room temperature to about 90° C. Sonication for durations from about 1 minute up to about 90 minutes may be used, if necessary, to aid in the dissolution of the PAEs or PIs. The homogeneous solutions are applied to a substrate and the volatile solvents are allowed to evaporate. The substrate may be held at atmospheric pressure or under vacuum. The substrate may be heated to expedite evaporation of the solvent. The heating may occur in steps, or be performed at one temperature. Once the solvent has been evaporated, the substrate is then heated to effect thermal imidization of the solution cast film. The heating may occur in a step-wise fashion or may occur at a fixed temperature up to about 350° C. The films are held at temperatures above about 250° C. for durations from about 30 minutes to about 240 minutes, depending on the monomer used in the polymerization. For example, and in no way to limit the invention, once the homogeneous solution has been applied to the substrate, the substrate could be placed in vacuum and heated to 100° C. for an hour, at 200° C. for an hour, and then at 300° C. for an hour to from a solid film. These thermally imidized films are thermally stable to temperatures in excess of about 400° C. to about 600° C., or more. It is well known that perylene and naphthalene derivatives have high decomposition temperatures.

Films may be cast that range from about 10 nm to about 1 cm. The optimal thickness is dependent on the desired application, but the invention allows for formation of the film at any thickness between about 10 nm to about 1 cm. The thin films have thermal, optical, electrical, electro-optical, and electrochemical properties which may be useful in the preparation of devices such as, but not limited to organic electronics, organic photovoltaics, flexible and/or transparent thin films, electro-optically active materials, dye-sensitized solar cells, bulk heterojunction cells, light emitting diodes, and various organic electronics. The resulting imides and polyimides can be designed to have high temperature stability to be compatible with high temperature processing potentially allowing the integration of the thin films into standard semiconductor processing approaches.

In another embodiment of the invention, an insoluble and intractable, thermally stable imide-functionalized film of particular compositions can be produced. The way this film is produced is through a soluble precursor. That soluble precursor contains imide precursors (aliphatic ester and aryl amide functional groups adjacent to each other). Upon thermal treatment, the ester and amide react with each other to form an aryl imide with concomitant loss of the alkyl group as an alcohol.

In yet another embodiment, the imide becomes part of the main chain as in the production of polyimides containing PTDA or NTDA. In this case, the soluble material is a poly (aryl amide) with pendent alkyl ester functional groups that confer solubility. Upon thermal treatment the material becomes a true polyimide where the imide functional group links each repeat unit along the main chain.

In a further embodiment, the imide becomes a pendent functional group on a material that has aryl-aryl bonds (a conjugated molecule/polymer) along the main chain. The pendent alkyl ester and pendent aryl amide groups confer solubility allowing solution processing to form a film. In this case, thermal processing results in loss of the alkyl ester as an alcohol and formation of a pendent imide group. The resulting film has material properties that include being thermally stable, insoluble, intractable, and with improved chain-chain packing which results in improved electronic properties.

In another embodiment, it is recognized that the final film, or fiber, cannot be directly produced because it would be insoluble and intractable not allowing the material to be made. However, the present invention provides a method that allows the preparation of soluble precursors to the desired materials in film form. The precursors can be used in solution with any solvent in which they are soluble, can be converted to films or fibers, and then can be thermally treated to result in the final desired structures. There are two types of materials: 1) the imide group is part of the linking group between connecting units (PTDA and NTDA polyimides or even smaller molecules/oligomers containing PTDA or NTDA) and 2) the imide is a pendent group to aryl-aryl coupled units, where the imide is part of an aryl (phenyl, naphthyl) or heteroaryl group (thiophene, or other). The alkyl ester is the important component for the solubility. The alkyl ester needs to be long enough to confer solubility but short enough that upon loss as an alcohol it is easily removed from the system. That means probably longer than butyl and probably shorter than decyl with hexyl being a good tradeoff. The alkyl ester could also be branched or contain other functional groups to improve solubility.

EXAMPLES

The following examples are provided to illustrate certain embodiments of the invention and are not to be construed as limitations on the invention, as set forth in the appended claims.

Example 1

Reagents and Solvents 1,4,5,8-naphthalenetetracarboxylic dianhydride (NTDA) (1), 3,4,9,10-perylenetetracarboxylic dianhydride (PTDA) (2) and 4,4'-oxydianiline (ODA) were obtained from Sigma Aldrich Chemical Co.; PTDA was dried under vacuum at 110° C. for 12 h while NTDA and ODA were purified by sublimation twice. Methanol and ethanol were refluxed over molecular sieves, 1-hexanol and 2-ethyl hexanol were distilled under N2; dimethyl sulfoxide (DMSO) was purified by distillation under reduced pressure over calcium sulfate. Pyridine (Py) was distilled from potassium hydroxide pellets. Triphenyl phosphite (TPP) was purified by repeatedly washing with saturated NaOH, saturated NaCl solution and finally with distilled water, followed by vacuum distillation. Lithium chloride (Aldrich) was dried under vacuum at 150° C. overnight. Deuterated dimethyl sulfoxide was dried using molecular sieves. All glass-wares were flame dried before use.

PTDA and NTDA Containing Monomer Synthesis

Figure 11:
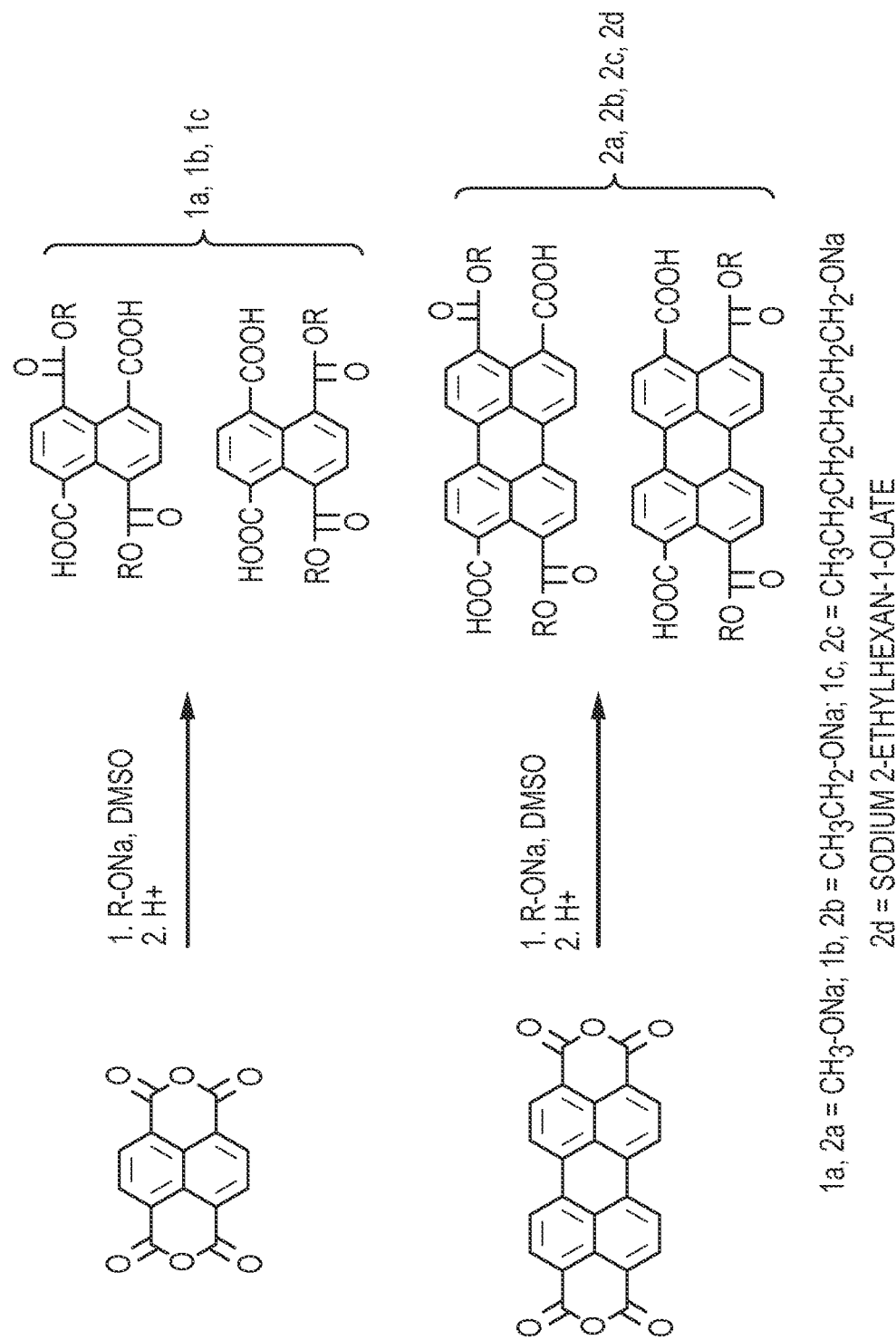
FIG. 11: illustrates an example of the synthesis of diester-diacids of PTDA and NTDA.

The methyl, ethyl and hexyl diester-diacids of NTDA (1a), (1b), and (1c) respectively were prepared following FIG. 11. Freshly cut sodium was dissolved in respective alcohol till all of the sodium metal dissolved. The excess alcohol was removed by rotary evaporation. Freshly prepared sodium alkoxide were reacted with NTDA dissolved in respective alcohol in a two-necked round bottomed flask equipped with a reflux condenser, nitrogen inlet and a stir-bar for 6 hours. The alcohol was removed under vacuum. The resulting solid was treated with excess aqueous HCl to convert the sodium salt to corresponding diester-diacid. The precipitate was then washed with excess of distilled water and dried in vacuum overnight. The methyl, ethyl and hexyl diesters (1a), (1b), and (1c) respectively were found to be soluble in most of the organic solvents and two spots were observed in thin layer chromatography (TLC) performed on MERCK TLC plates for the sodium salts using deionized water as the mobile phase.

Synthesis of di-esters of naphthalene-1,4,5,8 tetracarboxylic dianhydride (NTDA)

Synthesis of di-methyl ester of NTDA (1a)

Sodium alkoxide of methanol (0.0540 g, 0.001 mol) and NTDA (0.2000 g, 0.0005 mol) were reacted by the procedure as described above using methanol as solvent yielding 0.1641 g (98.79%) of (1a).

Nuclear magnetic resonance (NMR) spectrometry was used to verify the composition and purity of the product. The NMR spectrum is characterized by: 1H NMR (500 MHz, DMSO-d6, TMS) 4.21 (s, 6H), 8.8-9.5 (m, 4H).

Synthesis of di-ethyl ester of NTDA (1b)

Sodium alkoxide of ethanol (0.0680 g, 0.001 mol) and NTDA (0.2000 g, 0.0005 mol) were reacted by the same procedure as described above using ethanol as solvent yielding 0.1762 g (97.83%) of (1b).

Nuclear magnetic resonance (NMR) spectrometry was used to verify the composition and purity of the product. The NMR spectrum is characterized by: 1H NMR (500 MHz, DMSO-d6, TMS) 1.20 (t, 6H), 4.25 (s, 4H), 8.70-9.40 (m, 4H).

Synthesis of di-hexyl ester of NTDA (1c)

Sodium alkoxide of hexanol (0.1265 g, 0.001 mol) and NTDA (0.2000 g, 0.0005 mol) were reacted by the same procedure as described in above using 1-hexanol as solvent yielding 0.2294 g (97.09%) of (1c).

Nuclear magnetic resonance (NMR) spectrometry was used to verify the composition and purity of the product. The NMR spectrum is characterized by: 1H NMR (500 MHz, DMSO-d6, TMS) 1.00 (t, 6H), 1.30-1.45 (m, 12H), 4.28 (m, 4H) 7.25 (m, 4H), 8.90-9.45 (m, 4H).

Synthesis of di-esters of perylene-3,4,9,10 tetracarboxylic dianhydride (PTDA)

The methyl, ethyl, hexyl and 2-ethylhexyl diester-diacids of PTDA (2a), (2b), (2c) and (2d) respectively were prepared following FIG. 11. The methyl and ethyl diester-diacids of PTDA (2a) and (2b) was prepared by refluxing PTDA in the respective alcohol and refluxing for 20 hours. The suspension was then cooled and filtered. The resulting red solid was treated with excess aqueous HCl to convert the sodium salt to corresponding diester-diacid. The precipitate was then washed with excess of distilled water and dried in a vacuum overnight. The hexyl and 2-ethylhexyl diester-diacids (2e), (2d) were prepared using the following procedure. Freshly cut sodium was dissolved in respective alcohol till all of the sodium metal dissolved. The excess alcohol was removed by rotary evaporation. Freshly prepared sodium alkoxide were reacted with PTDA suspended in respective alcohol in a two-necked round bottomed flask equipped with a reflux condenser, nitrogen inlet and a stir-bar for 24 hours. The suspension was then cooled and filtered off. The resulting red solid was treated with excess aqueous HCl to convert the sodium salt to corresponding diester-diacid. The precipitate was washed with excess of distilled water and dried in vacuum overnight. The hexyl and 2-ethylhexyl diester-diacids (2c)

and (2d) respectively were found to be soluble in polar aprotic solvents like NMP, and DMSO. Two spots were observed in thin layer chromatography (TLC) for performed on MERCK TLC plates for the sodium salts of using deionized water as the mobile phase.

Synthesis of di-methyl ester of perylene-3,4,9,10 tetracarboxylic acid (2a) (PTDA)

The diester was prepared by suspending PTDA (0.1961 g, 0.0005 mol) in 20 mL of methanol, following the same procedure as described above yielding 0.2200 g (96.40%).

Infrared (IR) analysis was used to verify the composition and purity of the product. The IR spectrum is characterized by: (cm$^{-1}$) 3324, 2969 (O—H str, acid); 1690 (C=O str, acid, ester); 1448 (aromatic C=C str); 1299 (C—O—C str, ester); 1148, 1088 (C—O str); 857, 847, 806 (aromatic).

Synthesis of di-ethyl ester of perylene-3,4,9,10 tetracarboxylic acid (2b) (PTDA)

The diester was prepared by suspending PTDA (0.1961 g, 0.0005 mol) in 20 mL of ethanol, following the same procedure as described above yielding 0.2390 g (98.67%).

Infrared (IR) analysis was used to verify the composition and purity of the product. The IR spectrum is characterized by: (cm$^{-1}$) 2878 (O—H str, acid); 1672.5 (C=O str, acid, ester); 1501, 1459 (aromatic C=C str); 1294, 1262 (C—O—C str, ester); 1171, 1108 (C—O str); 857, 805, 837 (aromatic).

Synthesis of di-N-hexyl ester of perylene-3,4,9,10 tetracarboxylic acid (2c) (PTDA)

Sodium alkoxide of hexanol (0.1961 g, 0.001 mol) and PTDA (0.1961 g, 0.0005 mol) were reacted by the same procedure as described above using 1-hexanol as solvent yielding 0.2903 g (92.36%).

Infrared (IR) analysis was used to verify the composition and purity of the product. The IR spectrum is characterized by: (cm$^{-1}$) 3341 (O—H str, acid); 3120, 2968 (C—H str, hexyl); 1690 (C=O str, acid, ester); 1499 (C=C str); 1299 (C—O—C str, ester); 1148, 1088 (C—O str); 860, 837 (aromatic).

Nuclear magnetic resonance (NMR) spectrometry was used to verify the composition and purity of the product. The NMR spectrum is characterized by: 1H NMR (500 MHz, DMSO-d6' TMS) 0.79 (t, 6H), 1.25 (m, 10H), 1.65 (m, 3H), 4.2 (m, 3H) 7.25 (m, 4H), 7.45-8.00 (m, 8H).

Synthesis of di-2-ethy hexyl ester of perylene-3,4,9,10 tetracarboxylic acid (2d)

Sodium 2-ethylhexan-1-ol (0.1522 g, 0.001 mol) and PTDA (0.1961 g, 0.0005 mol) were reacted by the same procedure as described in above using 2-ethyl hexanol as solvent yielding 0.3300 g (96.40%).

Infrared (IR) analysis was used to verify the composition and purity of the product. The IR spectrum is characterized by: (cm$^{-1}$) 3341 (O—H str, acid); 3129,2900 (C—H str); 1690.5 (C=O str, acid, ester); 1510 (C=C str); 1289 (C—O—C str, ester); 1161, 1090 (C—O str); 886, 837 (aromatic).

Nuclear magnetic resonance (NMR) spectrometry was used to verify the composition and purity of the product. The NMR spectrum is characterized by: 1H NMR (500 MHz, DMSO-d6' TMS) 0.89-0.91 (t, 12H), 1.26-1.34 (d, 12H), 1.59 (q, 4H), 4.26 (m, 4H), 7.96-8.50 (m, 8H).

TABLE 1

Synthesis of diester-diacids of PTDA and NTDA

| Monomers | Alcohol [R] | Time [h] | $R_f{}^a$ | Solubility in various solvents[b] | | | | |
|---|---|---|---|---|---|---|---|---|
| | | | | NMP | DMSO | THF | DMAc | DMF |
| 1a | Methanol | 6 | 0.6, 0.7 | ++ | ++ | − | ++ | ++ |
| 1b | Ethanol | 6 | 0.5, 0.8 | ++ | ++ | − | ++ | ++ |
| 1c | 1-Hexanol | 6 | 0.6, 0.7 | ++ | ++ | − | ++ | ++ |
| 2a | Methanol | 20 | ND[c] | − | − | − | − | − |
| 2b | Ethanol | 20 | ND[c] | − | − | − | − | − |
| 2c | 1-Hexanol | 24 | 0.6, 0.7 | ++ | ++ | − | − | − |

[a]Sodium salts of 1a-c, 2c using de-ionized H$_2$O as mobile phase.
[b]The qualitative solubility was tested with 1-2 mg of monomer in 1 mL of stirred solvent.
[c]ND—Not Determined due to insolubility in all solvents.
NMP—N-methyl-2-pyrrolidone.
DMAc—N,N-dimethylacetamide.
DMF—N,N-dimethylformamide.
DMSO—dimethyl sulfoxide.
THF—tetrahydrofuran.
++ = Soluble at room temperature.
− = Insoluble even on heating.

Formation of the Polyamide-Ester (PAE) Derived from the di-N-hexyl Ester of NTDA and ODA under Yamazaki-Higashi conditions (IA)

A mixture of (1c) (0.3309 g, 0.0012 mol), ODA (0.2471 g, 0.0012 mol), lithium chloride (4 g), TPP (2.5470 g, 0.0018 mol), pyridine (8.4 mL) and DMSO (25 mL) was heated under stirring at 80° C. for 16 h under nitrogen. A highly viscous pale yellow solution was obtained. When cooled, the reaction mixture was dropped into 500 mL of methanol, and the precipitated polymer was washed thoroughly with water and methanol, collected by filtration and dried.

Formation of the Polyamide-Ester (PAE) Derived from the Di-N-hexyl Ester of PTDA and ODA Under Yamazaki-Higashi Conditions (IIA)

A mixture of (2c) (1.4857 g, 0.0024 mol), ODA (0.5005 g 0.0025 mol), lithium chloride (4.0 g), TPP (2.547 g, 0.0018 mol), pyridine (8.4 mL) and DMSO (25 mL) was heated under stirring at 80° C. for 16 h in a nitrogen atmosphere. The viscosity increased to a point where the stir-bars no longer stirred. When cooled, the reaction mixture was dropped into 500 mL of acetone, and the precipitated polymer was washed thoroughly with water and methanol, collected by filtration and dried.

Formation of the Polyamide-ester (PAE) Derived from the Di-2-ethyl hexyl Ester of PTDA and ODA Under Yamazaki—Higashi Conditions (IIB)

The PAE was synthesized following the procedure as above, using a mixture of (2d) (1.5763 g, 0.0024 mol), ODA (0.5005 g, 0.0025 mol), lithium chloride (4.0 g), TPP (2.547 g, 0.0018 mol), pyridine (8.4 mL) and DMSO (25 mL) was heated under stirring at 80° C. for 16 h in a nitrogen atmosphere. When cooled, the reaction mixture was dropped into 500 mL of acetone, and the precipitated polymer was washed thoroughly with water and methanol, collected by filtration and dried.

Preparation of Polyimide Films from Polyamide-Ester

Figure 12:
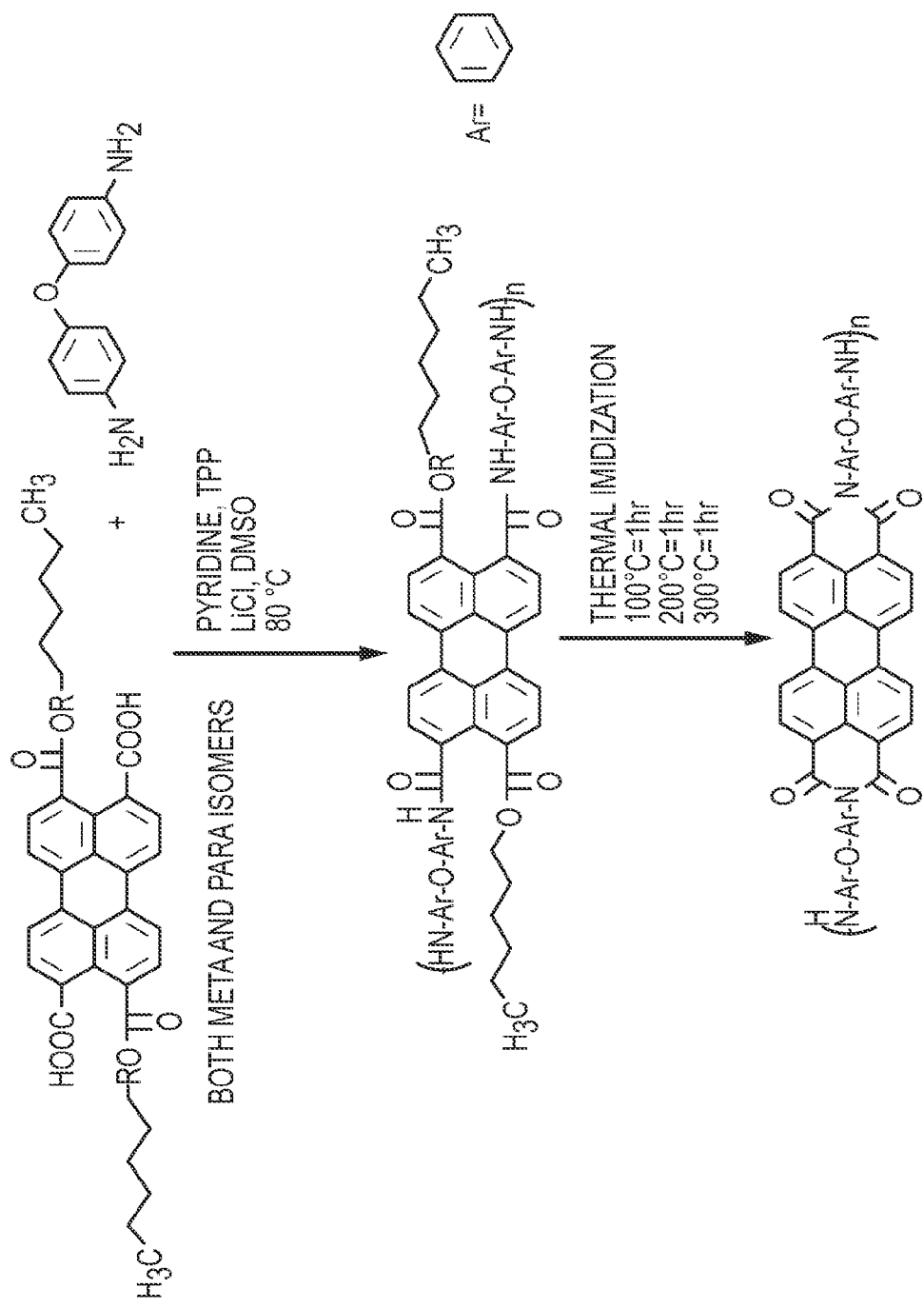
FIG. 12: illustrates an example of the proposed mechanism for polymer synthesis.

Solutions of 5-8 wt % of naphthalene polyamide-esters and solutions of 2-5 wt % of perylene polyamide-esters were dissolved in DMSO. The homogeneous solution was poured on a glass slide, which was placed under vacuum and heated to 100° C. for an hour, at 200° C. for an hour and at 300° C. for an hour to form a solid film. These films on cooling were stripped from the glass surface by soaking in water. The polymer films were further dried in vacuo for 24 hours. Not to bound by any theory, the proposed mechanism for polymer synthesis is shown in FIG. 12.

Characterization

Infrared analysis was performed using Nicolet 4700—Thermo Electron Corporation. The 1H Nuclear Magnetic Resonance (NMR) spectra was obtained by means of 500 MHz JEOL liquid state spectrometer. Titrations were carried out on Orion Star Series Meter. The UV-Vis spectroscopy were recorded on Beckman Coulter DU 800 at a concentration of $1\times10-3-5\times10-3$ mole/dm3. Fluorescence analysis were performed on Photon Technology International QuantaMaster 40 fluorescence spectrometer. Cyclic voltammetry experiments were carried out on Gambry Reference 600™ Potentiostat/Galvanostat/ZRA. Films for thermal analysis of about 15-20 um thick were cast from DMSO heated to 300° C. in a step wise fashion and held for 30 min at this temperature. Glass transition temperatures, taken as the midpoint of the change in slope of the heat flow rate, were measured on a Perkin Elmer Differential Scanning Colorimeter instrument at a heating rate of 10° C. per min. Isothermal and variable temperature (5° C. per min heating rate) thermal gravimetric analysis (TGA) measurements were performed on a Seiko TGA SSC/5200 under $N_2$.

Experimental Results and Discussion

Monomer Synthesis

The synthesis route employed to obtain diester-diacids (1a, 1b, 1c, 2a, 2b, 2c, 2d) has been illustrated in FIG. 11. Perylene diesters could not be synthesized by refluxing them in the corresponding alcohols due to the insolubility of PTDA in all organic solvents. The reaction of both perylene and naphthalene dianhydrides with sodium alkoxide of respective alcohols yielded the diester-diacids as confirmed by NMR spectroscopy. The presence of two isomers, meta and para were indicated by the appearance of two spots in TLC plates. The presence of alkyl group improves the solubility of perylene moiety and provides (a/an) handle to keep them in solution. The two acid groups were available for the condensation reaction with diamines, resulting in polyamide-ester solution which could be precipitated in acetone and reconstituted again in DMSO or NMP.

Synthesis of polyamide-esters (PAE's) and polyimides (PI's)

The hexyl diester-diacids of both naphthalene and perylene (1c, 2c, 2d) were polymerized with ODA under Yamazaki-Higashi amidation conditions at lower temperatures (80° C.) to obtain the polyamide-ester; the precursor to the polyimide. The PAE was then precipitated in methanol and acetone for naphthalene and perylene polyamide-esters respectively; which was re-dissolved back into DMSO and NMP, making it convenient to cast them as films. Thermal imidizations of the solution cast films for thermal analysis of about 20 μm thick were cast from DMSO heated to 300° C. in a step wise fashion and held for 30 min at this temperature. These films were found to be flexible. Lower reaction temperatures were employed to prevent imide ring-closure seen at higher temperatures. The lower temperatures also have the effect of keeping the PAE in solution.

TABLE 2

Solubility behavior and thermal properties of the polyamide-esters and polyimides

| Polymers | Solubility in various solvents[c] | | | | | Tg (° C.)[d] | Char yield (wt. %)[f] |
|---|---|---|---|---|---|---|---|
| | NMP | DMSO | m-cresol | THF | DMAc | | |
| (IA) NTDA-ODA[a] | ++ | ++ | +− | − | ++ | ND[e] | 29.8 |
| (IA) NTDA-ODA | − | − | − | − | − | 270 | 62 |
| (IIA) PTDA-ODA[b] | ++ | ++ | +− | − | − | ND[e] | 30.8 |
| (IIA) PTDA-ODA | − | − | − | − | − | 296 | 54 |

[a,b]Polyamide-ester (hexyl) of NTDA-ODA, and PTDA(hexyl)-ODA.
[c]The qualitative solubility was tested with 2 mg of polymer in 1 mL of stirred solvent.
NMP—N-methyl-2-pyrrolidone.
DMAc—N,N-dimethylacetamide.
DMSO—dimethyl sulfoxide.
THF—tetrahydrofuran.
++ = Soluble at room temperature.
+− = Soluble on heating.
− = Insoluble even on heating.
[d]Midpoint temperature of the baseline shift on the second DSC heating trace (rate = 20° C./min).
[e]Not determined.
[f]Residual weight percentage at 800° C. in nitrogen.

Solubility and Thermal Properties

Figure 3:
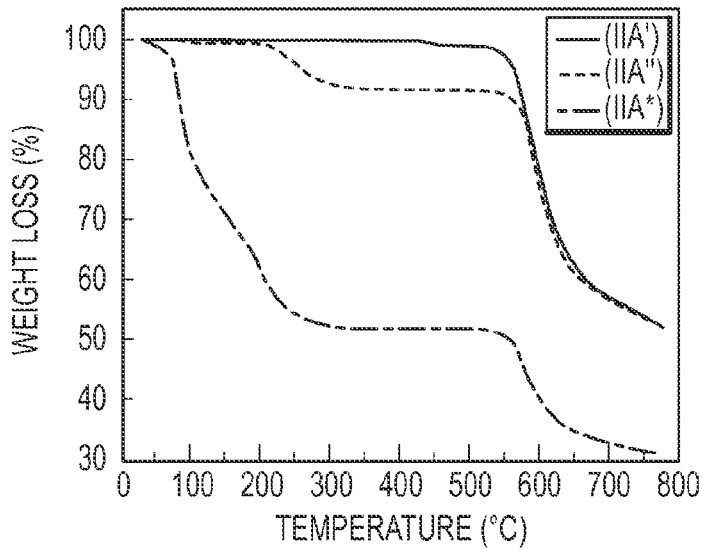
FIG. 3: depicts thermal analysis of polyimides and polyamide-esters of (IIA)

The solubility of the polyamide-esters and polyimides were tested qualitatively as summarized in Table 2. The polyamide-esters of both naphthalene and perylene were found to be soluble in DMSO and NMP at room temperature on sonication for 30 min and in m-cresol on heating to 80° C. The polyimide's, on the other hand were found to be insoluble in all solvents even on heating which could be attributed to the rigid structure on ring closing. Typical TGA curves for the PI and the PAE are shown [see FIG. 3]. Thermal analysis of the polyamide esters was performed to quantify the loss of alcohol and obtain the temperature at which imidization or ring closing completes. The temperature was increased in steps wherein the polyamide-ester (IIA)* was held for specific time intervals at 100, 160, 200, 220, 240, 260, and 300° C. in the Seiko TGA SSe/5200. A weight loss of 29% was observed around 160-180° C. that could be attributed to hexanol; no further weight loss was observed after 260° C. [see FIG. 3]. Furthermore TG analysis of both naphthalene and perylene PAE shows complete imidization below 300° C. [see FIG. 3]. The films that were previously thermally imidized under vacuum up-to 250° C. were found to show 12% weight loss between 200-400° C. indicating incomplete imidization. However, PAE's which were thermally imidized to 300° C. and held at that temperature for 30 min externally showed less than 5% up-to 500° C. on thermal analysis indicating completion of imidization. The degradation of the back bone can be observed beyond 700° e as shown in FIG. 3. It is well known that perylene and naphthalene derivatives have high decomposition temperatures. Similar weight loss were observed for the naphthalene PAE due to loss of alcohol and both perylene and naphthalene polyimides which were thermally imidized externally at 300° C. were having high char yields. From DSC analyses, glass transition temperatures (Tg) of both the naphthalene and the perylene polyimides were between 277-290° C. The high glass transition temperature and stability of the PI's up to 500° C. are attributed to the rigid planar structure of peryleneimide and naphthalimide moiety.

FT-IR Characterization of the Polyamide-Esters and the Polyimides

Figure 4:
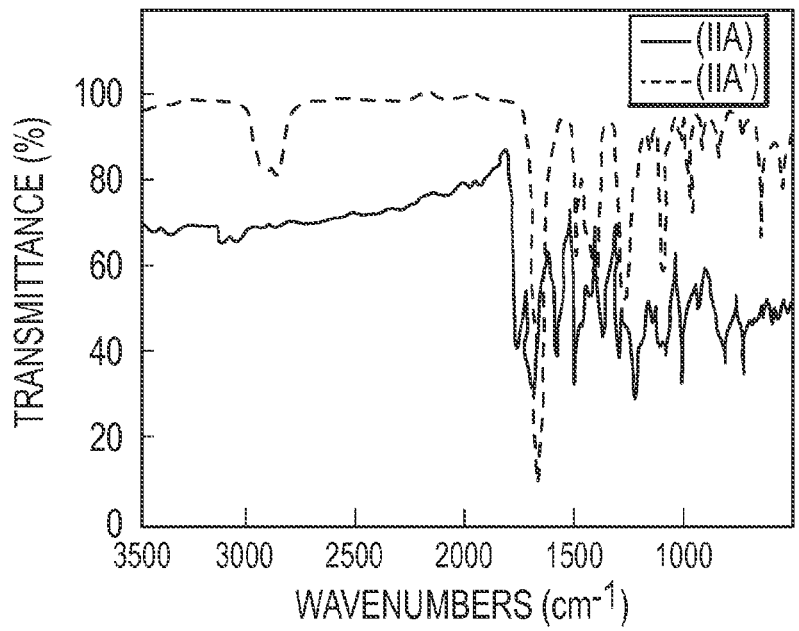
FIG. 4: depicts FT-IR spectroscopy of perylene PAE and PI.

The polyamide-esters and the final polyimides were characterized using FT-IR spectroscopy to confirm ring closing in thermally cured polyimides. FIG. 4 shows the FT-IR spectrum of PAE (IIA), obtained by precipitating in methanol and drying overnight under vacuum and the final PI of (IIA) treated thermally to 300° C. The PAE shows N—H bands at 3200-3400 $cm^{-1}$ and the amide stretching at 1672.5 $cm^{-1}$ typical for open ring structures in polyamide acids. All the thermally cured PI's showed characteristic imide ring absorption in the range of 1770-1780 $cm^{-1}$ (asymmetrical c=o imide stretching), 1720-1730 $cm^{-1}$ (symmetrical c=o imide stretching) and 720-730 $cm^{-1}$ (imide ring deformation). The disappearance of amide peak and the appearance of the imide peaks corresponding to 1702 $cm^{-1}$, 1591.8 $cm^{-1}$, 1380 $cm^{-1}$ and 730.3 $cm^{-1}$ confirms the complete cyclization of the PAE resulting in final PI. The IR spectroscopy conclusively proves that imidization is complete when the films were held at 300° C. for 30 min.

Optical Properties

The optical properties such as absorption and emission, properties of the prepared naphthalene and perylene diesters were analyzed by UV-Vis and photoluminescence (PL) spectroscopies in solution. The optical properties of solutions of polyamide-esters and the thermally cured polyimides in the solid state were also studied. The effect of excitation wavelength and concentration on PL properties and was also examined.

Ultraviolet-Visible Investigations

Figure 5:
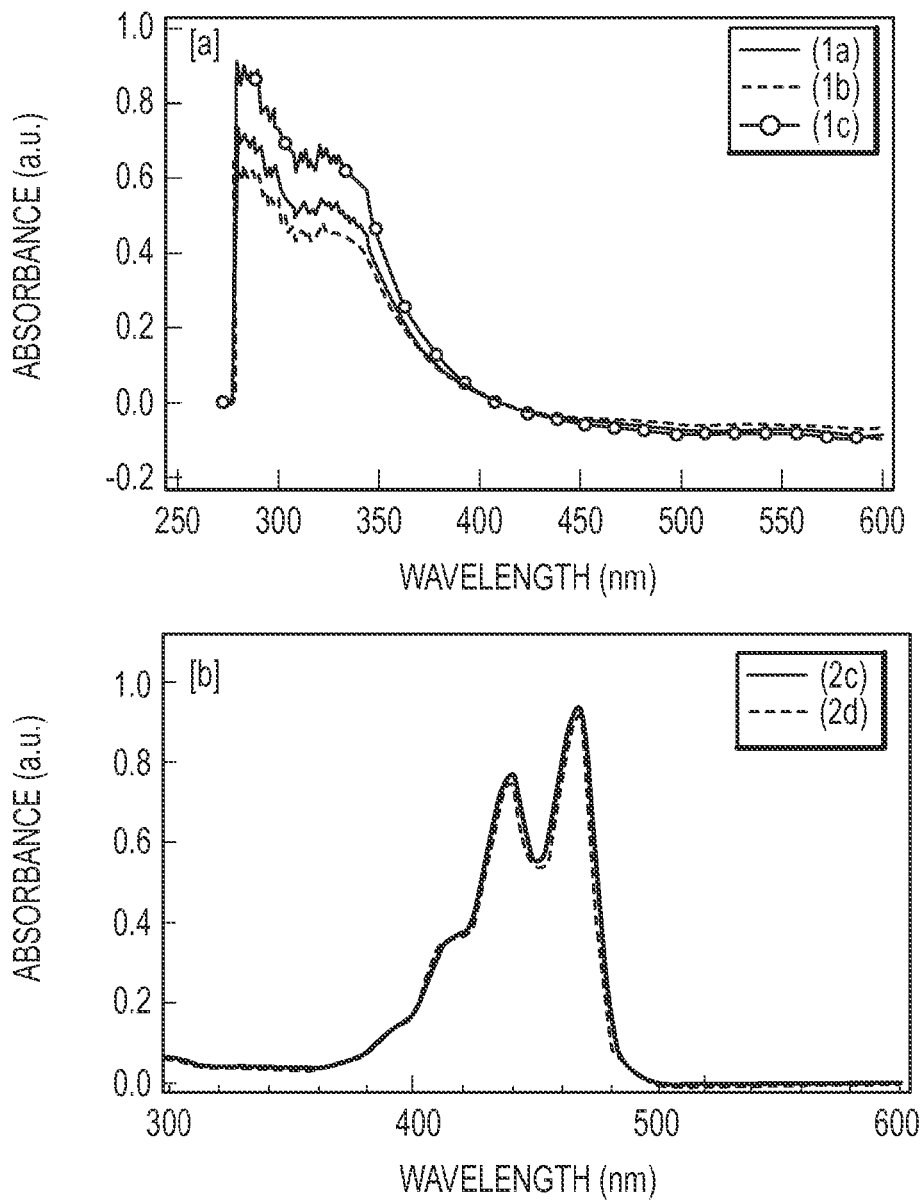
FIG. 5: depicts UV-Vis spectroscopy of diester-diacids of naphthalene and perylene.
Figure 6:
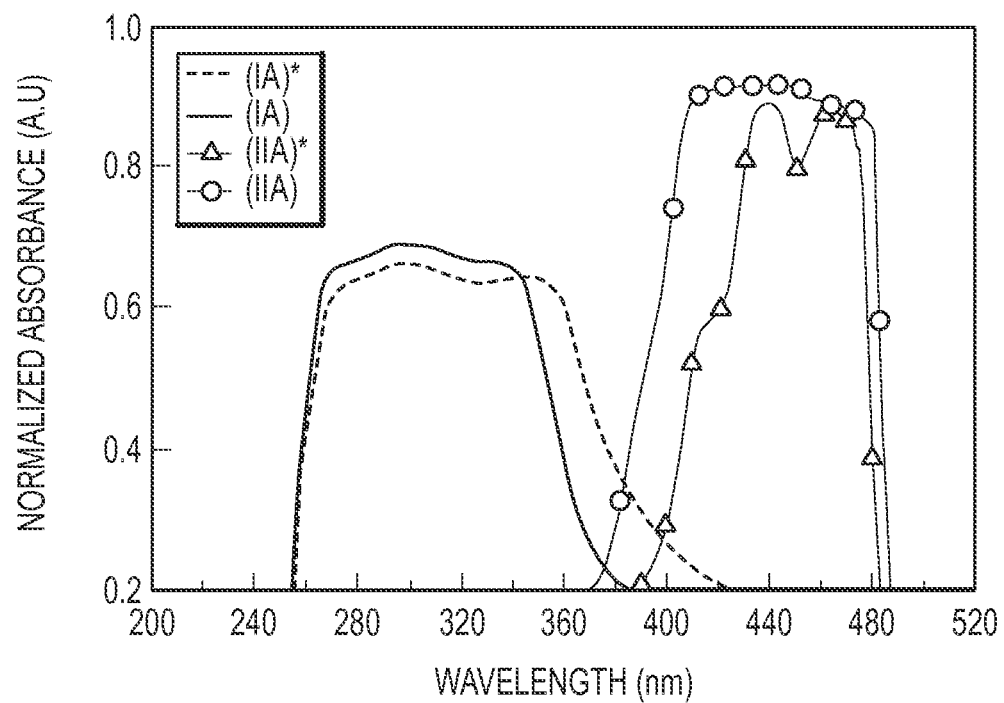
FIG. 6: depicts UV-Vis spectroscopy of PAE and PI of (Ia) and (IIA)

The UV absorption spectra of the naphthalene and perylene diesters-diacids dissolved in DMSO are shown in FIG. 5. The naphthalene diesters [see FIG. 5(a)] have a weak band with a maximum located around 285 nm and a structured band at lower energy at about 325 nm typical for naphthalene moiety, which are attributed to the π-π* transition in the naphthalene tetracarboxylic diimide. It can be observed from the plot that the chain length causes no major change in the absorption maximum for the diesters. The perylene diester-diacids [see FIG. 5(b)] absorption spectra are identical, which exhibit a fine structure with one shoulder and two peaks and at 412, 440, and 465 nm, respectively. It is obvious that the alkyl chain length has no influence on the absorption spectra in solution, which is in agreement with earlier observations perylene tetraesters. The absorption spectra of the polyamide-esters (dissolved in DMSO) and the final polyimides (as a film) are shown in FIG. 6. The PAE's of naphthalene, (IA)* has two peaks at 300 and 350 nm which could be attributed to the naphthalene core. The PAE of perylene, (IIA)*, had peaks at 440 and 460 nm typically seen in perylene incorporated diimides. Subsequently, the absorption spectra of compounds (IA) and (IIA) in evaporated films on quartz slides were recorded. Unlike to the solution spectra, the absorption spectra of the films are broad and structureless. Bathochromic shift was observed between the polyamide esters in DMSO and the final polyimides. This may be caused by the chemical structure change from the open ring structure to the closed imide formation and possible aggregation during film formation.

The optical energy band gap ($E_g^{opt}$) was calculated using the following equation:

$$E_g^{opt} = hc/\lambda_{offset} \quad (1)$$

where h is plank's constant, c is light velocity and $\lambda_{offset}$ is the absorption edge wavelength of the optical absorption spectra. The values of $E_g^{opt}$ was found to be 4.86 eV for poly naphthalimide (IA) and 1.19 eV for poly peryleneimide (IIA).

Photoluminescence Properties

The factors that can mainly influence the photoluminescence (PL) properties of organic compounds are from chemical structure as well as from experimental conditions. In this work, the influence of two factors on the emission spectra was considered: changing the excitation wavelength, the physical form of the polymer; the precursor in solution state and the final polyimide as a film coated on quartz slide.

The influence of the excitation wavelength on PL properties, that is, on the position of emission band maximum and intensity of emitted light is shown. [see FIG. 7(a)]. First, DMSO solutions of the polyamide-esters of naphthalene (IA)* at concentrations of $1\times10^{-4}$ mol/L were excited with different wavelengths to obtain the conditions that provide the best fluorescence spectrum, that is, with the highest relative luminescence intensity. The emission spectra were then recorded under these excitation wavelengths. Similar procedures were carried out for PAE of perylene (IIA)*. For naphthalene polyamide-esters, excitation under different wavelength exhibited a single emission peak for the higher wavelength. However the lower wavelength excitation, Ex=330 nm gave an emission peak with a small shoulder at lower wavelength and of lower intensity. In comparison for the PAE of perylene (IIA)*, [see FIG. 7(b)] highest PL intensity was observed under Ex=445 nm. In first two cases, two emission bands were observed, and a single emission band for the higher wavelength excitation was noticed as shown. [see FIG. 7(b)] Changes in both the emission position and its intensity with an increase of excitation from 446 to 520 nm were observed. A bathochromic shift of emission position along with longer excitation was detected. The highest PL intensity for PAE (IIA)* was observed under Ex=490 nm.

Additionally fluorescence characteristics of the polyimides (IA) and (IIA) were studied as films since they were insoluble in all solvents. The films were excited with a wavelength which gave the highest emission intensity in solution. A substantial red shift was observed with polyimides of (IA) and (IIA) compared to their emission behavior in DMSO as PAE's. This could be attributed to the structural change, wherein the polyimides have a closed ring structure and possible aggregation during the evaporation of the solvent.

Figure 13:
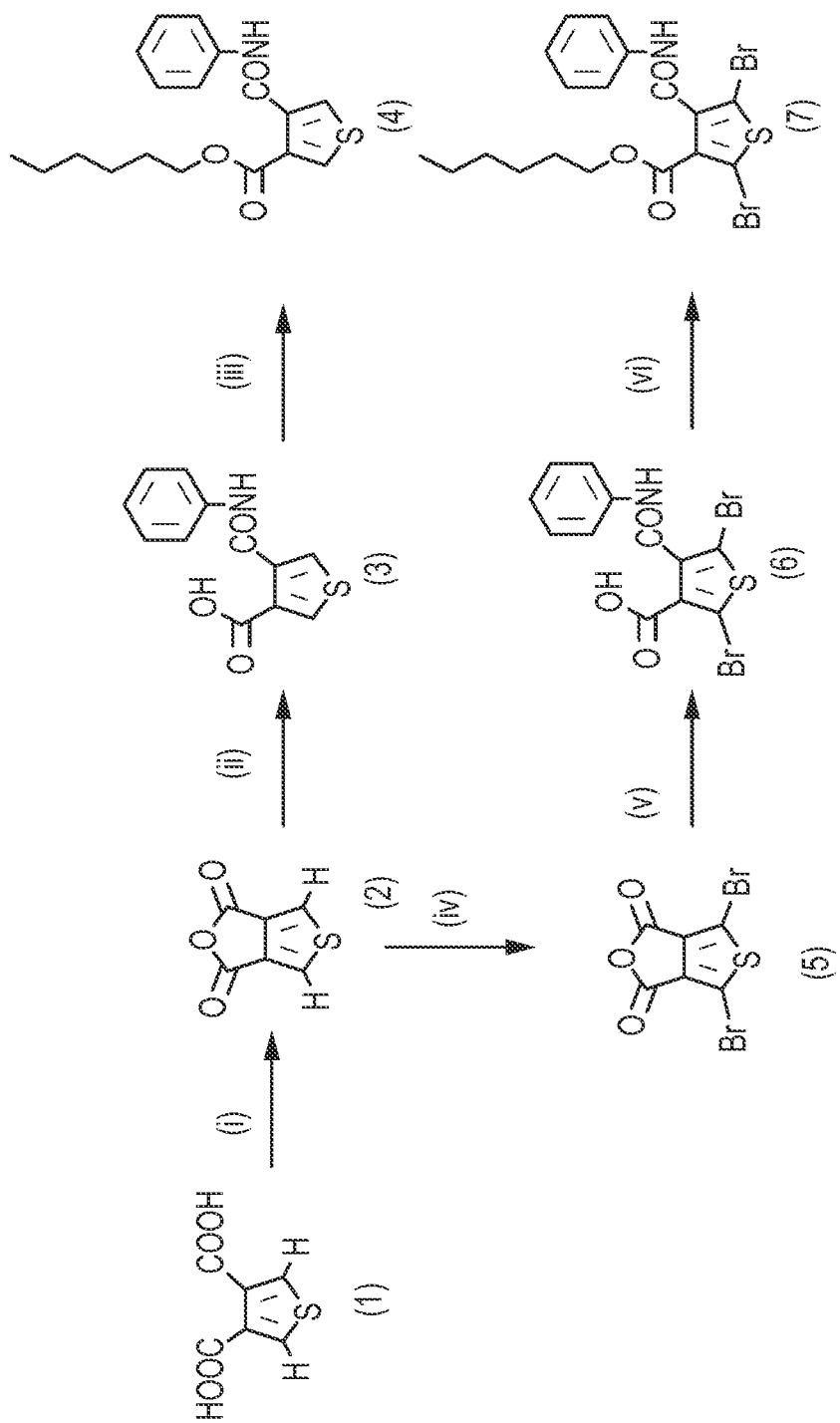
FIG. 13: illustrates an example of the synthesis of thiophene amide ester based monomers.

Synthetic Procedures for Pendent Amide Ester Pi-Conjugated Monomer Synthesis:

A representative procedure is illustrated in FIG. 13 for the synthesis of thiophene-based monomers.

Reaction (i) Illustrated in FIG. 13: Formation of 1H, 3H-Thieno[3,4-c] furan-1,3-dione, Compound (2) Illustrated in FIG. 13.

In a 250 mL single-neck round-bottom flask equipped with reflux condenser, 3,4-thiophenedicarboxylic acid (Frontier Scientific, 4.000 g, 0.02325 mol) was heated to 120° C. with acetic anhydride for 6 hours. The reaction was then cooled to room temperature and the solvent was removed under reduced pressure to yield a dark brown solid. The crude product was recrystallized from toluene to yield pale yellow needles in quantitative yield.

Nuclear magnetic resonance (NMR) spectrometry was used to verify the composition and purity of the product. The NMR spectra is characterized by: $^1$H NMR (500 MHz, d6-DMSO): δ 8.47 (s); $^{13}$C NMR (500 MHz, d6-DMSO): δ 156.2, 135.1, and 129.1; M.P 144-145.5° C.

Reaction (ii) Illustrated in FIG. 13: Formation of 4-(phenylcarbamoyl)thiophene-3-carboxylic acid, Compound (3) Illustrated in FIG. 13

In a 100 mL single-neck round-bottom flask, fitted with an addition funnel and condenser, compound (2) (3.7 g, 0.02400 mol) was dissolved in DMF (40 ml) and aniline (2.6821 g, 0.0288 mol) was added dropwise (over 10-15 min) to the stirred solution (exothermic, using addition funnel, under N$_2$). The reaction mixture was then heated to 140° C. overnight, cooled to room temperature, and then slowly precipitated into water. This crude amide-acid was filtered off and washed with cold hexanes. Yield 4.30 g.

Reaction (iii) Illustrated in FIG. 13: Formation of hexyl 4-(phenylcarbamoyl)thiophene-3-carboxylate, Compound (4) Illustrated in FIG. 13

In a single-neck round-bottom flask, fitted with a reflux condenser, compound (3) (4.26 g, 0.0172 mol) was refluxed in 40 mL 1-hexanol overnight, under N$_2$. The reaction was then cooled to room temperature and was concentrated under vacuum and cooled to get the product as a white solid. The product was recrystallized from acetone.

Nuclear magnetic resonance (NMR) spectrometry was used to verify the composition and purity of the product. The NMR spectra is characterized by: $^1$H NMR (500 MHz, d6-DMSO): δ 0.77-0.81 (t, 3H), 1.09-1.29 (m, 6H), 1.48-1.54 (t, 2H), 4.11-4.14 (t, 2H), 7.05-7.09 (t, 1H), 7.30-7.34 (t, 2H), 7.69-7.71 (d, 2H), 7.96 (s, 1H), 8.31 (s, 1H), and 10.37 (s, 1H); $^{13}$C NMR (500 MHz, d6-DMSO): δ 13.84, 21.87, 25.09, 28.01, 30.84, 64.64, 119.30, 123.32, 128.58, 128.75, 131.60, 134.16, 138.67, 139.26, 162.17, and 162.50.

Reaction (iv) Illustrated in FIG. 13: Formation of 4,6-dibromothieno[3,4-c]furan-1,3-dione, Compound (5) Illustrated in FIG. 13

Compound (2) (2.5008 g, 0.0162 mol) and glacial acetic acid (30 mL) were added to a 250 mL flask with a stirring bar. Bromine (5 mL) was added drop-wise. The mixture was stirred overnight. Aqueous sodium bisulfite solution was added until the reddish color disappeared. The mixture was cooled, filtered and washed with 50 mL of cold deionized water. Finally, compound (5) was obtained as a greyish-green solid (2.162 g).

Nuclear magnetic resonance (NMR) spectrometry was used to verify the composition and purity of the product. The NMR spectra is characterized by: $^{13}$C NMR (500 MHz, d6-DMSO), δ (ppm): 160.51, 135.2, and 115.89.

Reaction (v) Illustrated in FIG. 13: Formation of 2,5-dibromo-4-(phenylcarbamoyl)thiophene-3-carboxylic acid, Compound (6) Illustrated in FIG. 13

Compound (5) (2 g, 0.0064 mol) and aniline (0.7152 g, 0.00768 mol) were reacted in a procedure similar to compound (3). Yield 1.9623 g.

Reaction (vi) Illustrated in FIG. 13: Formation of 2,5-dibromo-4-(phenylcarbamoyl)thiophene-3-carboxylic acid, Compound (7) Illustrated in FIG. 13

Compound (6) (1.5 g, 0.00370 mol) was reacted with 1-hexanol (25 mL) in a procedure similar to compound (4).

Synthesis of Polymers

Representative Procedure for the Polymerization

Hexyl 4-(phenylcarbamoyl)thiophene-3-carboxylate (4) (0.2949 g, 0.000890 mol), hexyl 2,5-dibromo-4-(phenylcarbamoyl)thiophene-3-carboxylate (7) (0.2952 g, 0.000890 mol), palladium catalyst (4% mol), ligand (8% mol) and Cs2CO3 (162.9 mg; 0.50 mmol) were put in a microwave vial with a magnetic stirring bar. Tetrahydrofuran (1 mL) was added and sealed. 5 cycles of freeze pump thaw was done and the reaction was kept at 120 degree Celsius for 48 hours. The whole mixture was cooled to room temperature and poured in 500 mL of cold methanol. The precipitate was filtered and dissolved in THF and precipitated again. This procedure was repeated 3 times to remove small molecules.

Nuclear magnetic resonance (NMR) spectrometry was used to verify the composition and purity of the product. The NMR spectra is characterized by $^1$H NMR (500 MHz, d6-DMSO): δ 0.71 (3H), 1.34-1.43 (m, 6H), 2.04 (2H), 3.38-4.16 (2H), 6.64-8.25 (5H). GPC Mn 17421, PDI 2.34.

Example 2

Synthesis of P2 (AI-201)

The procedure followed was similar to compound P1 with Hexyl 4-(phenylcarbamoyl)thiophene-3-carboxylate (4) (0.2952 g, 0.000890 mol) and 5,5'-diiodo-2,2'-bithiophene (0.3720 g, 0.000890 mol).

UV-Vis Characterization

Polymers were analyzed for UV-Vis properties and presented in FIG. 6. The −1 samples are in the amide ester form. The −2 samples are for films after thermal treatment to form the imide pendent groups.

Thermogravimetric Analysis

Figure 7:
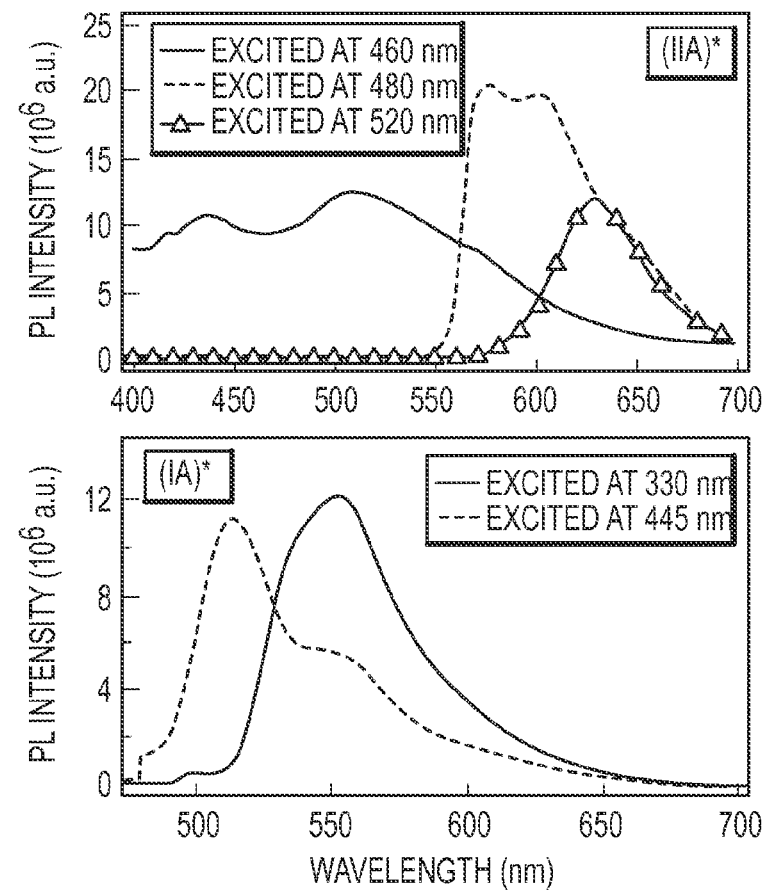
FIG. 7: depicts fluorescence spectroscopy of PAE and PI of (IA) and (IIA)
Figure 7:
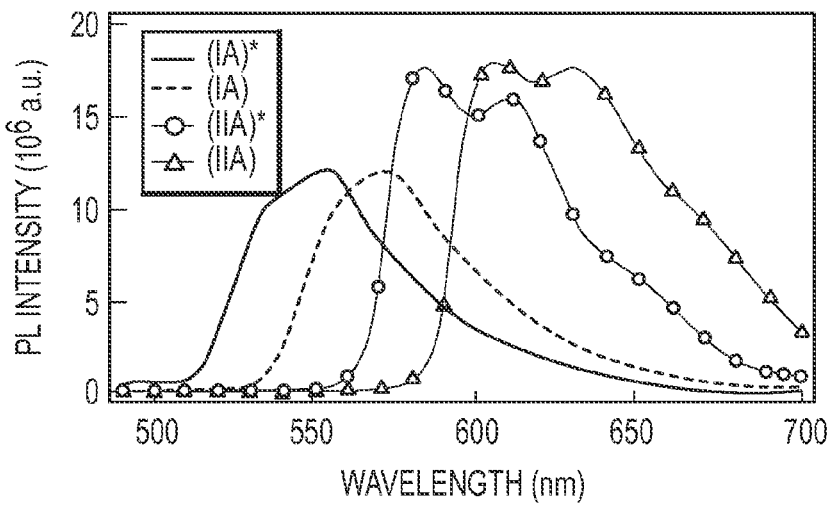
Figure 8:
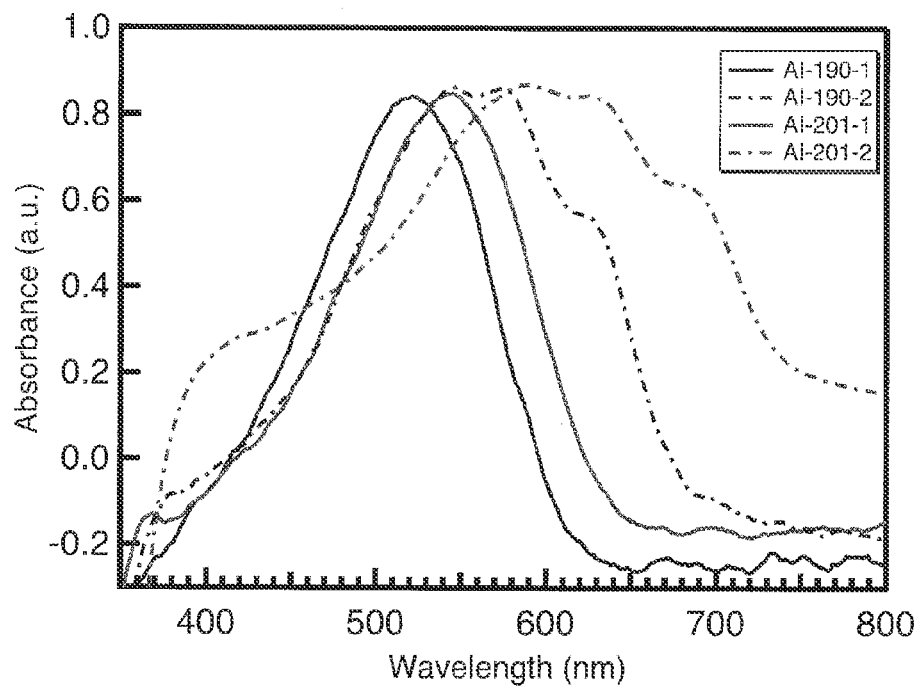
FIG. 8: depicts a UV-Vis analysis of polymer examples.
Figure 9:
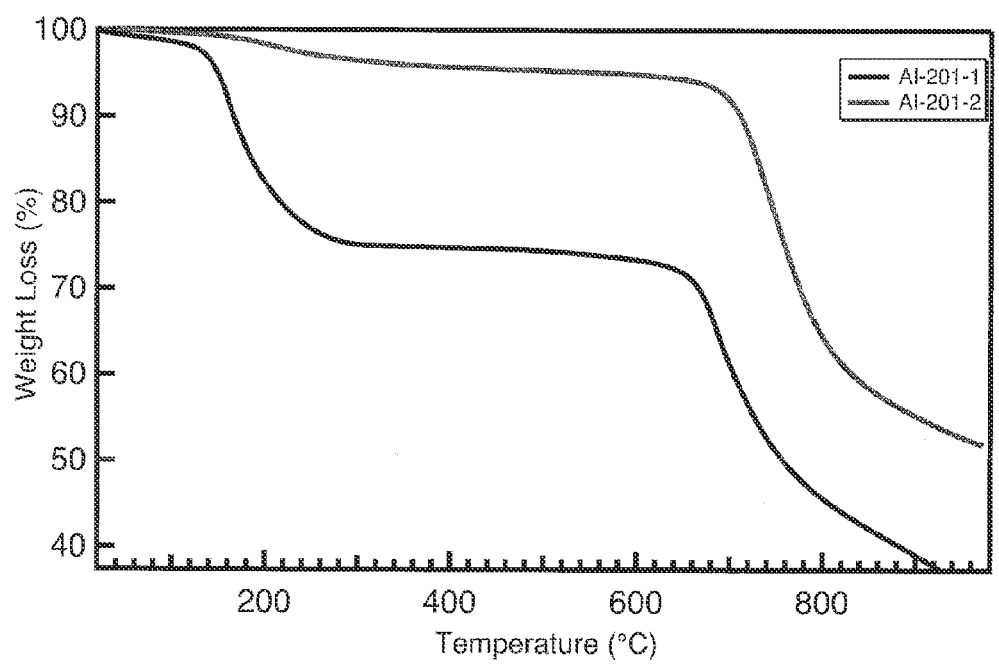
FIG. 9: depicts thermogravimetric analysis of polymer examples showing imidization and hexanol weight loss and resulting thermally stable material.

Polymer (AI-201) produced from 5,5'diiodo-2,2'bithiophene and (4) was analyzed by thermogravimetric analysis and presented in FIG. 7. The weight loss of the imide formation and formation of the hexyl alcohol can be observed to occur between 180° C. and 300° C. (AI-201-1). After thermal treatment to form the imidized polymer, thermogravimetric analysis shows only minimal further weight loss presumably from some residual hexyl alcohol and high thermal stability to above 600° C.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method for making an imide rigid material, comprising:
   providing a starting material, comprising an ester and an adjacent carboxylic acid group;
   reacting the carboxylic acid group of the starting material to form a soluble material comprising an amide with the ester, wherein the ester group confers solubility to the soluble material; and
   heating the soluble material to produce the imide rigid material.

2. The method of claim 1, wherein the starting rigid material is an amide.

3. The method of claim 1, wherein the ester and amide functionalized soluble material comprises at least one of an alkyl ester and an alkoxyalkyl ester.

4. The method of claim 3, wherein the alkyl ester comprises a carbon group selected from the group consisting of a methyl group, an ethyl group, a butyl group, a propyl group, a heptyl group, a hexyl group, an octyl group, a nonyl group, and a decyl group.

5. The method of claim 2, wherein the amide is a polyamide.

6. The method of claim 5, wherein the polyamide comprises a component selected from the group consisting of perylene, naphthalene, and phenylene.

7. The method of claim 1, further comprising an apparatus, wherein the apparatus comprises a substrate and the rigid material, wherein the apparatus is selected from the group consisting of an organic electronic apparatus, an organic photovoltaic apparatus, a dye-sensitized solar cell, a bulk heterojunction cell, and light emitting diode.

8. The method of claim 3, wherein the alkoxyalkyl ester is selected from the group consisting of a methoxyethyl, an ethoxyethyl, a propoxyethyl, and a methoxyethyloxyethyl.

9. The method of claim 1, further comprising:
preparing a homogeneous ester amide solution comprising a solvent and the ester and amide functionalized soluble material;
heating the homogenous ester amide solution to a fixed temperature; and
maintaining at the fixed temperature for a predetermined time to form at least one fiber or at least one film.

10. The method of claim 1, wherein an amide in the ester and amide functionalized soluble material is an aryl amide.

11. The method of claim 1, wherein a temperature is increased to the fixed temperature incrementally.

12. The method of claim 1, wherein the fixed temperature is above 100° C. and less than about 350° C.

13. A method to form an imide rigid material, comprising:
providing a molecule comprising an ester and an adjacent amide group;
reacting the molecule to form a conjugated structure, wherein the ester and the adjacent amide group are pendent to the conjugated structure, and wherein the ester pendent to the conjugated structure confers solubility to the conjugated material; and
heating the conjugated material to form the imide rigid material.

14. The method of claim 13, wherein the amide group is an aryl amide.

15. The method of claim 14, wherein the aryl amide is selected from the group consisting of a phenyl group, an acene group, oligophenyl group and a heteroaryl group.

16. The method of claim 13, wherein the ester group that is pendent comprises a carbon group selected from the group consisting of a methyl group, an ethyl group, a butyl group, a propyl group, a heptyl group, a hexyl group, an octyl group, a nonyl group, and a decyl group.

17. The method of claim 13, wherein the conjugated material comprises at least one of thiophene, phenylene, naphthalene, furan, and pyrrole.

18. The method of claim 13, wherein the ester that is pendent and the amide that is pendent are adjacent to each other.

19. The method of claim 13, wherein the ester group that is pendent is selected from the group consisting of a methoxyethyl, an ethoxyethyl, a propoxyethyl, and a methoxyethyloxyethyl.

20. The method of claim 13, further comprising an apparatus, wherein the apparatus comprises a substrate and the imide rigid material, wherein the apparatus is selected from the group consisting of an organic electronic apparatus, an organic photovoltaic apparatus, a dye-sensitized solar cell, a bulk heterojunction cell, and light emitting diode.

* * * * *